US006421560B1

(12) United States Patent
Yoo

(10) Patent No.: US 6,421,560 B1
(45) Date of Patent: Jul. 16, 2002

(54) DEVICE FOR GUIDING SPOTS FOR ACUPUNCTURE AND STIMULATION METHODS THEREOF

(76) Inventor: Tae Woo Yoo, 807, 1-Dong, Hanyang Apt., 32-5, Banpo-Dong, Seocho-Ku Seoul (KR)

(*) Notice: Subject to any disclaimer, the term of this patent is extended or adjusted under 35 U.S.C. 154(b) by 0 days.

(21) Appl. No.: 09/481,763

(22) Filed: Jan. 11, 2000

(30) Foreign Application Priority Data

Jul. 29, 1999 (KR) .............................................. 99-30981

(51) Int. Cl.[7] ........................... A61B 5/04; A61H 39/02

(52) U.S. Cl. ....................................... 600/548; 128/907

(58) Field of Search ......................... 600/548; 128/907; 607/2, 46

(56) References Cited

U.S. PATENT DOCUMENTS 5,195,517 A * 3/1993 Chen
5,366,379 A * 11/1994 Yang et al.
6,022,314 A * 2/2000 Wei
6,132,218 A * 10/2000 Benja-Athon

* cited by examiner

*Primary Examiner*—Jeffrey R. Jastrzab
(74) *Attorney, Agent, or Firm*—Richard M. Goldberg

(57) ABSTRACT

A device for guiding spots for acupuncture including: a CPU controlling storage or output of data according to a control signal by a user; the 1st storage printing stored image data according to a control signal of the CPU; a character data producer printing character data according to a control of the CPU; a RGB data producer transforming data stored in the 1st storage unit to image data according to a control of the CPU; and a video signal transformation transforming output shape of output signal of the character data producer or RGB data producer.

6 Claims, 4 Drawing Sheets

IN PREPARATION (RED)

IN PREPARATION (RED)

IN PREPARATION (GREEN)

DEVICE FOR GUIDING SPOTS FOR ACUPUNCTURE AND STIMULATION METHODS THEREOF

BACKGROUND OF THE INVENTION

1. Field of the Invention

The present invention relates to a device for guiding spots for acupuncture and stimulation methods thereof, and more particularly, to a device for guiding spots for acupuncture and stimulation methods displayed on a static TV display or a monitor for a convenient use.

2. Description of the Prior Art

In general, acupuncture is a traditional medical science including wisdom and experience of ancestors in three oriental nations (Korea, China and Japan). Korean ancestors have talked about first acupuncture, second moxibustion and third medication. The saying means that if somebody has an illness, it is the first step to take acupuncture needle stimulation, and if it doesn't work, then to take a moxibustion and the last step is medication. It shows how deeply our ancestors depended on acupuncture therapy.

But we have made little of our traditional acupuncture in today's modernized society. Therefore, the system of acupuncture has been abolished and this kind of medical science is almost abandoned except as possessed by only a few.

Today's acupuncture therapy is a new kind of acupuncture developed and researched further by Dr. Tae Woo Yoo for the first time recently in Korea and provided to all over the world. A hand is a micro-universe reflecting a human body and all our internal organs have their corresponding areas in a palm. Therefore, pains in some areas of a body would be eliminated by just stimulating their corresponding areas in the palm. And also, acupuncture therapy is so easily taught by everybody and very effective that anyone who has just a little experience in the method can use it as a home treatment. According to the acupuncture therapy, we feel a pain if spirits and blood produced in the five viscera and the six entrails are not provided into the organs in a body appropriately.

And an illness is attributed to reasons as follows. First is a case that functions of the five viscera and the six entrails are not in a good harmony (if there is a declination). Second is a case that a person has a stiff body. Third is a case that a person has inappropriately fixed bones. In those cases, the most effective method to improve normal flow of spirits is acupuncture therapy, and there are some other therapies such as, ring therapy using five fingers, corresponding therapy in which painful spots are stimulated, and spirits and pulse therapy in which functions of internal organs are fixed by prescriptions according to physical constitutions.

Recently, the acupuncture therapy includes seoam pellets, T-pellets, magnetic needles, electronic beam as well as acupuncture needles. However, those who don't have expertise in these fields have difficulties in finding spots for acupuncture and curing them without consulting acupuncture-related special books.

SUMMARY OF THE INVENTION

The present device was designed to solve the problems described as above. Therefore, an object of the present invention is to provide a device displaying spots for acupuncture and stimulation methods thereof on a static TV display or a monitor.

Another object of the present invention is to provide a device for guiding spots for acupuncture and stimulation methods of yumpa therapy, a cyber method without acupuncture instruments.

A feature of the present invention is a device for guiding spots for acupuncture comprising: a CPU controlling storage and output of data according to a control signal by a user; the 1st storage printing stored image data according to a control signal of the CPU; a character data producer printing character data according to a control of the CPU; a RGB data producer transforming data stored in the 1st storage unit to image data according to a control of the CPU; and a video signal transformation transforming the output shape of an output signal of the character data producer or RGB data producer.

Another feature of the present invention is a device for guiding spots for acupuncture comprising: a level displaying an initial display of the guiding program of spots for acupuncture according to a control signal by a user; a level displaying stimulation details according to a control signal by a user; and a level displaying image information about spots for acupuncture in a palm according to a control signal by a user.

BRIEF DESCRIPTION OF THE DRAWINGS

The other objects and features of the present invention will be hereinafter explained in detail with reference to the accompanying drawings, wherein.

DESCRIPTION OF THE PREFERRED EMBODIMENTS

Figure 1:
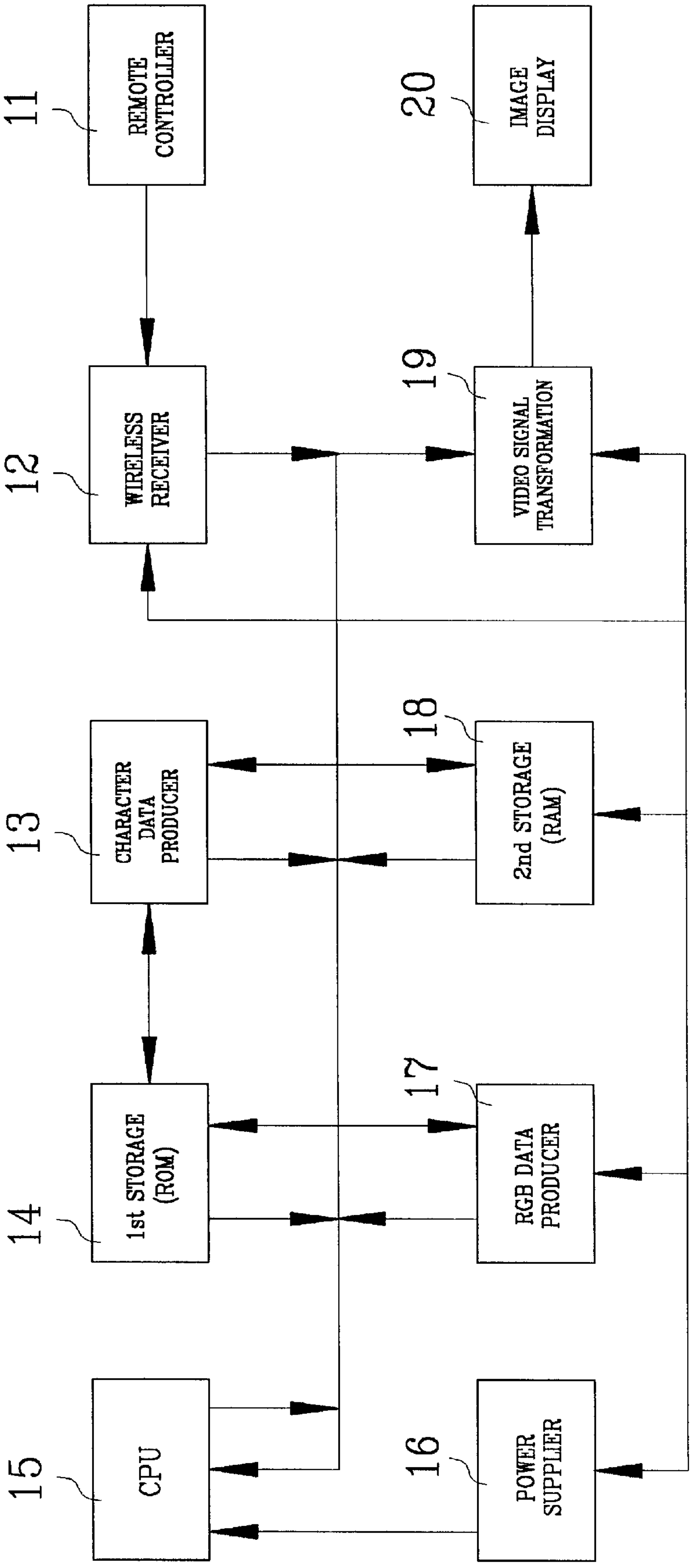
FIG. 1 is a block view forming a device for guiding spots for acupuncture and stimulation methods of the present invention.

As shown in FIG. 1, the device for guiding spots for acupuncture includes: a remote controller 11 controlling the device for guiding spots for acupuncture, a wireless receiver 12 receiving wireless signals sent by the remote controller 11, a CPU 15 controlling storage and output of data according to a control signal by the wireless receiver 12, a power supplier 16 supplying power required to operate the device for guiding spots for acupuncture, the 1st storage (ROM) 14 printing stored image data according to a control of the CPU 15, a character data producer 13 printing character data according to a control of the CPU 15, a RGB data producer 17 transforming data stored in the 1st storage into image data according to a control of the CPU 15, the 2nd storage, (RAM) 18 storing data outputted from the character data producer 13 and RGB data producer 17 temporarily, a video signal transformation 19 transforming a shape of the output signal of the 2nd storage 18 and an image display 20 displaying the output signal of the video signal transformation 19.

The 1st storage 14 includes information for guiding spots for acupuncture according to the present invention. The video signal transformation 19 changes the output signal of the 2nd storage 18 into 24 bit RGB input mode such as NTSC, PAL and so on. At this moment, 24 bit RGB data producer 17 decides resolution of a program of the device for guiding spots for acupuncture and prescription according to control signals from CPU 15 and horizontal or vertical oscillating signals from video signal transformation 19. Image display 20 is an image display device displaying a static image about spots for acupuncture and cure messages on a static TV or a monitor.

Figure 2:
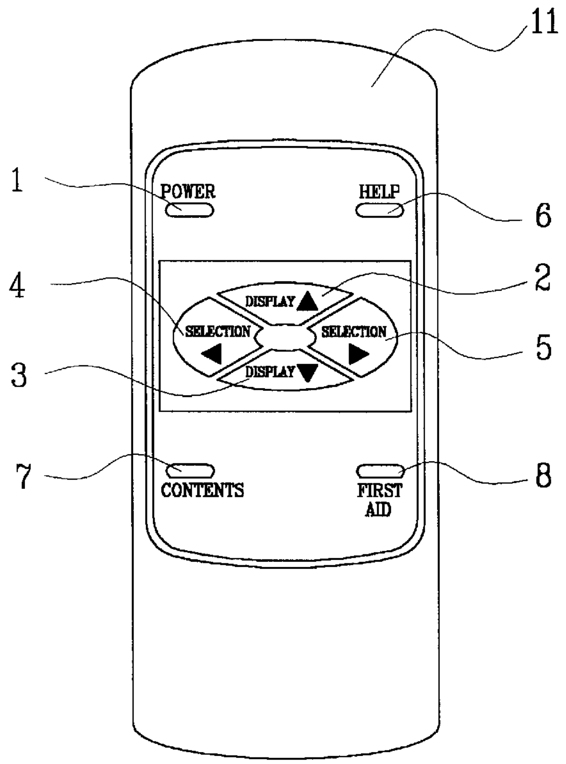
FIG. 2 is a flat view of a remote controller of the present invention.
Figure 3:
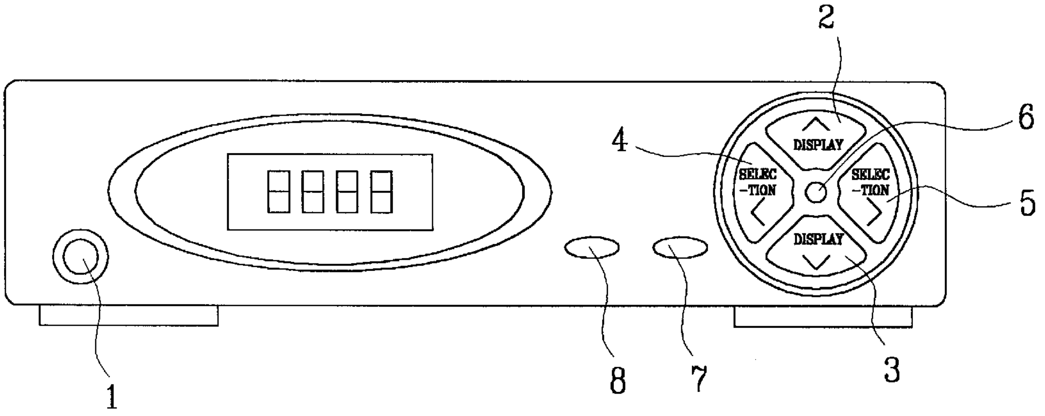
FIG. 3 is a front view of a device for guiding spots for acupuncture and stimulation methods of the present invention.
Figure 4:
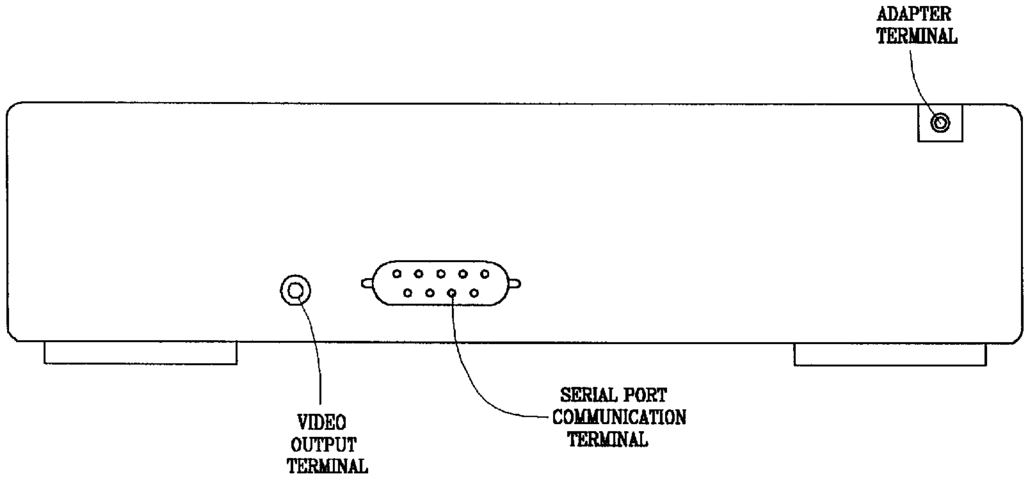
FIG. 4 is a rear view of a device for guiding spots for acupuncture and stimulation methods of the present invention.

As shown in FIG. 2, FIG. 3, and FIG.4, power 1 is a button for turning or off a device for guiding spots for acupuncture of the present invention.

Display ▲ 2 is a button used for searching for a symptom and transforming a display. If you want to use yumpa therapy, Yumpa therapy is available with just one more click. (If you want to escape from yumpa therapy, click one more time.)

Display ▼ 3 is a button for escaping from a selected symptom, and has functions opposite to Display ▲ 2, and is used for moving to a former display (Back). The button is also for escaping from yumpa therapy.

Selection ◀ 4 is a button used for selecting a symptom among listed contents displayed by pressing Display ▲ 2 and Display ▼ 3, and moves in a left or upper direction. The button is also used for moving into another spot in the spots description or yumpa therapy.

Selection ▶ 5 is a button used for selecting a symptom among listed contents displayed by pressing Display ▲ 2 and Display ▼ 3, and moving in a right or lower direction. The button is also used for gaining information about spots for acupuncture or moving into another spot in yumpa therapy.

Help 6 is used if you need descriptions about signals or positions of spots in the middle of using a prescription display. If you want to escape from Help, press Help 6. However, if you move into another spot, use Selection ◀ 4 or Selection ▶ 5 button.

Contents 7 is used for moving into the initial content in the middle of using a prescription display.

First aid 8 is used for moving directly into first aid prescription contents in case of an emergency or from any display. Use the remote controller 11, or operate with buttons of the device for guiding spots for acupuncture therapy of the present invention.

Figure 5:
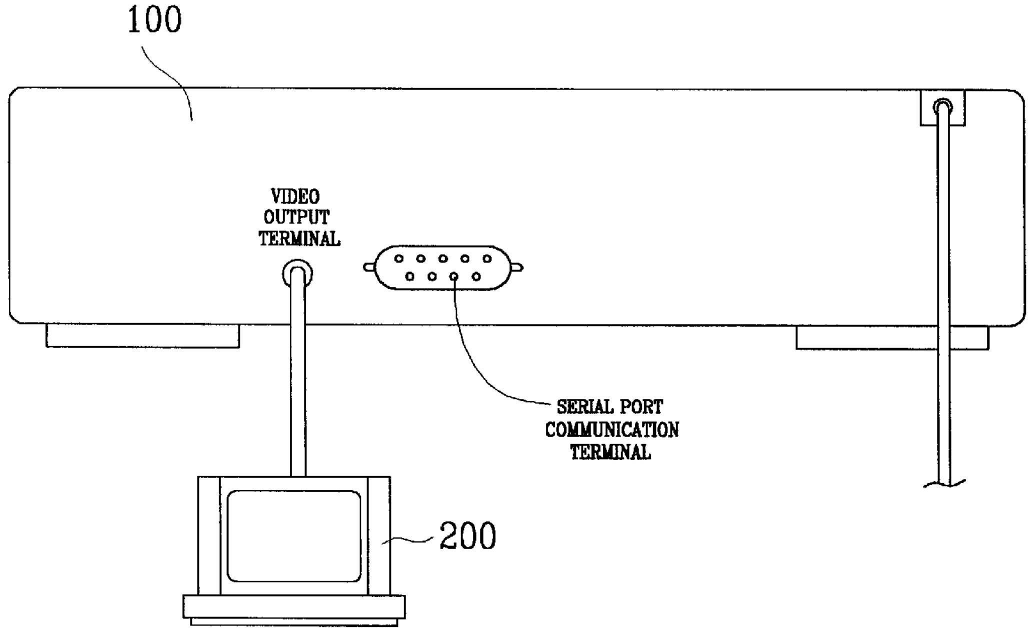
FIG. 5 is a view of a device for guiding spots for acupuncture and stimulation methods of the present invention combined with a TV.

As shown in FIG. 5, the video output terminal of the present invention 100 is connected with the image input terminal of TV 200. If there are plural image input terminals, make sure to connect with 'image' or 'image input' terminal.

After connecting as shown in FIG. 5, turn on the TV and press power 1 of the device for guiding spots for acupuncture or of the remote controller 11. In case that the TV 200 has a set (sound or image), change TV 200 into 'video' mode, using a TV/VIDEO transformation switch of the remote controller 11.

On the other hand, in case that the TV has some sets (sound or image), select an 'outside input' button of the remote controller 11.

After finishing preparation as above, you will face the initial display of the device for guiding spots for acupuncture.

Hereinafter, a possible use of the present invention is explained along with an accompanying drawing.

If you press Display ▲ 2 of the remote controller at the initial display, selection contents including "Where do you have a pain?", "Who is sick?", "What is an acupuncture needle?", "first aid", "Beauty/Health" are provided. If you select "where do you have a pain?", you can select parts which have a problem from the table 1 as below.

TABLE 1

| Item | body | contents |
|---|---|---|
| Where do you have a pain? | head | chronic headache, anemia, stress, all kinds of headaches, nausea, migraine, and so on |
| | ear | ringing, pain |
| | mouth | stomatitis, herpes, toothache |
| | shoulder | armpit, pain in collarbone, stiff shoulder |
| | stomach | hepatitis, hypersensitive colitis, gastroenteritis, cystitis, constipation, indigestion, food poisoning |
| | back | pain in back |
| | reproduction organ | erection impotence, frigidity, decrease of vaginal secretion, sexual impotence, urethritis |
| | arm | palsy or cramp in hand, eczema, housewife eczema |
| | leg | arthragia in knees, eczema, pain in feet, groin eczema, calf pain |
| | eye | conjunctivitis presbyopia, eye fatigue, tear, sty, amblyopia |
| | nose | hastis, ozena, snore, nose is stopped up, nose bleeding, nose drippings, |
| | neck | cough, phlegm, chronic bronchitis, hoarseness pharyngitis, tonsillitis |
| | breast | pain in ribs, high blood pressure, low blood pressure, costal pain, lack of mother's milk, breast-related diseases |
| | waist | high blood pressure, low blood pressure, costal pain, lack of mother's milk, breast-related diseases |
| | anus | anal fistula, hemorrhoids, proctocele, anal bleeding |
| | womb | leukcorrhea, infertility, menstrual pain, habitulal abortion, menstrual irregularity, vaginitis |
| | skin | discoloration of the face, freckle, rash, dermatitis, unerarm odor, acne |

If you select the item, "Who is sick?", you can choose one among a student, housewife, company employee and so on.

Also, if you select the item, "What is an acupuncture needle?", you can use information about cyber acupuncture needles, acupuncture-related instruments, correspondence therapy, 14 spirits and pulse, spots for acupuncture, and so on.

If you select the item, "first aid", you can go to emergency prescription contents immediately. The emergency prescription contents include infant acute convulsion, stupor, unconsciousness, shock, chest pain, food poisoning, high temperature, nose bleeding and so on.

Also, if you select the item, "Beauty/Health", the display is replaced with Beauty/Health contents immediately.

At this time, if you select one of the commands(hand transfer, hand needles, seoam moxibustion or yumpa therapy) with Selection ◀ 4, or Selection ▶ 5 button and then press Display ▲ 2 button, you can study spots for acupuncture on a palm or the back of the hand, or move into detailed descriptions about basic treatment instruments or yumpa therapy.

Second, in case that you have chronic headache, select the item, "Where do you have a pain?" with Selection ◀ 4, and Selection ▶ 5 buttons, and press Display ▲ 2 button.

Third, as chronic headache is a disease in a head, press head in the table 1 with Display ▲ 2 button.

Figure 6:
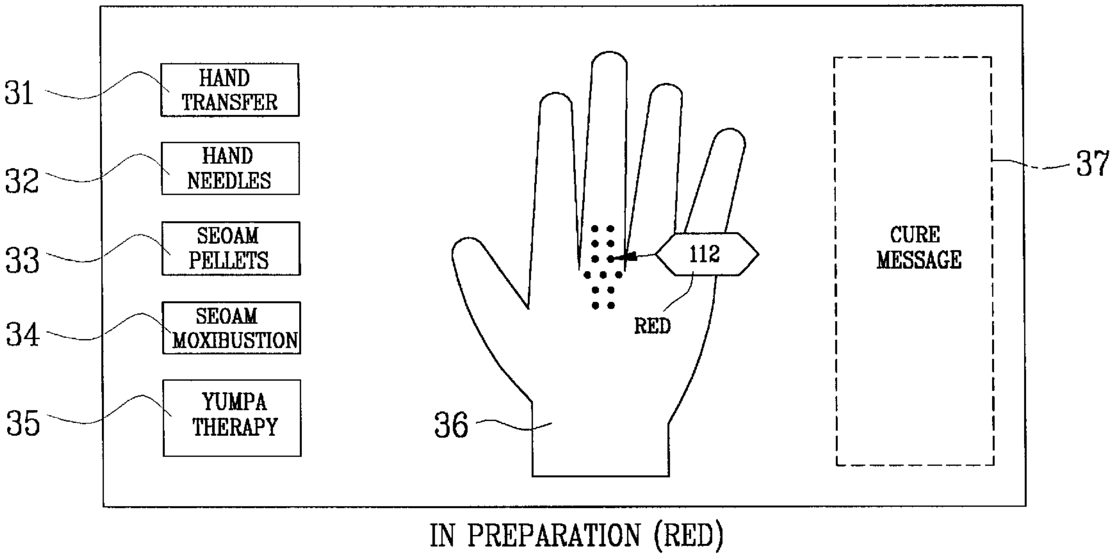
FIG. 6 and FIG. 7 are possible displays according to operations of the present invention.
Figure 7:
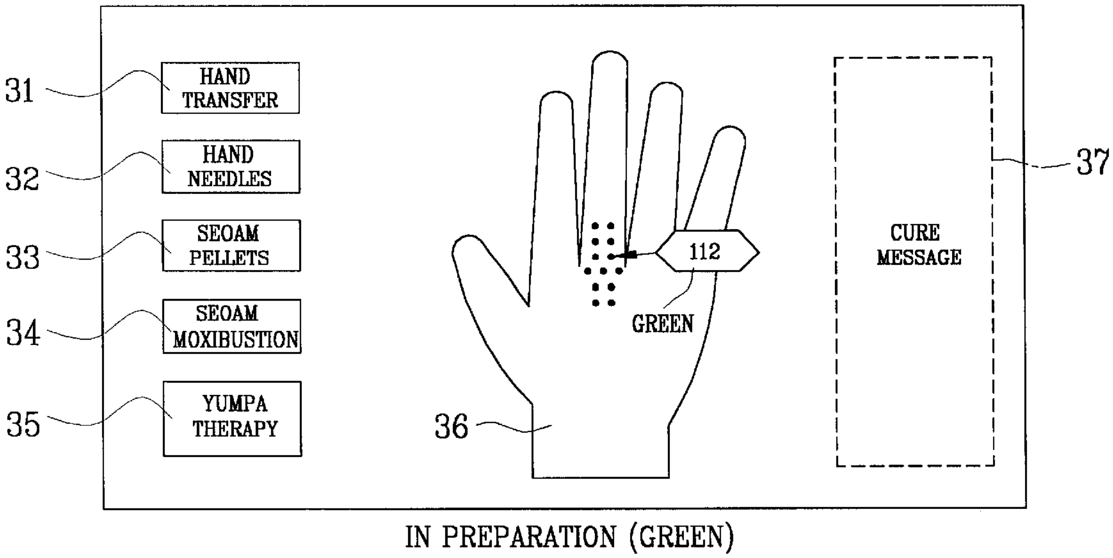

Fourth, if you press chronic headache with Display ▲ 2 button, spots and cure messages 37 in a hand shape 36 are provided in FIG. 6 and FIG. 7, respectively.

Fifth, you can treat chronic headache according to cure message in the right part of the display. If you need information about spots further, press Help 6, or Selection ◀ 4, or Selection ▶ 5 button. And if you want to escape from Help, press Help 6 one more time.

Sixth, kinds of prescriptions such as hand needles 32, seoam pellets 33, seoam moxibustion 34 and yumpa therapy 35 are provided in the left part. If you want to select yumpa therapy 35, select yumpa therapy 35 with Selection ◀ 4 or Selection ▶ 5, and press Display ▲ 2 button.

Seventh, you can go back to the initial display by keeping pressing Display ▼ 3 button or pressing Contents 7 button, if necessary.

Yumpa therapy is also used in traditional acupuncture therapy, correspondence therapy and 14 spirits and pulse. If you want to conduct yumpa therapy, you can move into yumpa therapy contents with Selection ◀ 4 or Selection ▶ 5. Press Display ▲ 2 button, and a "red" hand shape is provided as shown in FIG. 6. This is a state in which yumpa therapy is in preparation. Press Display ▲ 2 button one more time, and the hand shape is changed into "green" as shown in FIG. 7, and then yumpa therapy is available in that state. If you want to escape from yumpa therapy, press Display ▲ 2 button one more time and the hand shape is changed into red and the yumpa therapy is automatically abandoned.

Meanwhile, if you want to move into another spot, press Selection ◀ 4, or Selection ▶ 5 button after escaping from yumpa therapy using methods as above.

Also, if you want to implement Bosa therapy(therapy of increasing or decreasing spirits or blood), press Help 6 in the middle of yumpa therapy, and needles move upward from the bottom in order. At this moment, press Selection ▶ 5, and Bosa therapy of yumpa therapy is conducted.

Also, in case that you treat 14 spirits and pulse and various spots for acupuncture (12 myunghyul, gijunghyul, ohsuhyul, gimohyul, giyuhyul, palsunghyul), press "What is an acupuncture needle?", "Acupuncture therapy", "14 spirits and pulse and spots for acupuncture", "Spots for acupuncture" in the initial display of the device for guiding spots for acupuncture in order with Selection ◀ 4, Selection ▶ 5 button, or Display ▲ 2 button.

And, find out the item you want to choose in various spots for acupuncture (12 myunghyul, gijunghyul, ohsuhyul, gimohyul, giyuhyul, palsunghyul) with Selection ◀ 4 or Selection ▶ 5 button and press it with Display ▲ 2 button.

And find out yumpa therapy among hand transfer, hand needles, seoam pellets, seoam moxibustion and yumpa therapy with Selection ◀ 4 or Selection ▶ 5 button and press Display ▲ 2 button.

And, as yumpa therapy is made to stimulate the right part of the spot, stimulate the right part of the spot by pressing Display ▲ 2 button, and move into the left side by pressing Selection ◀ 4 button and Display ▲ 2 button. And then yumpa stimulation is conducted.

If you want to use Bosa therapy in yumpa therapy, decide the position of Bo therapy (increasing spirits or blood) and Sa therapy (decreasing spirits or blood) by pressing Help 6, when needle shape is red, and press Display ▲ 2 button. And then yumpa stimulation is conducted.

After finishing yumpa stimulation, go back to the initial display by pressing Display ▼ 3 or Contents 7 button on the remote controller.

As mentioned above, the present invention provides a device for guiding spots for acupuncture to enhance an effect of providing information about guiding spots for acupuncture and stimulation methods thereof, using a static image display device. Accordingly, those who need acupuncture therapy can use acupuncture therapy or yumpa therapy conveniently, using spots for acupuncture provided in the device for guiding spots according to the present invention.

What is claimed is:

1. A device for guiding spots for acupuncture comprising:

a central processing unit (CPU) for controlling storage and output of data according to a control signal by a user;

a first storage unit, connected with said CPU and including data stored therein for guiding spots for acupuncture, for outputting said stored data according to a control signal of said CPU;

a character data producer for outputting character data according to a control of said CPU;

a RED GREEN BLUE (RGB) data producer for transforming data output by said first storage unit to image data according to a control of said CPU; and a video signal transformation for transforming output signals of said character data producer and said RED GREEN BLUE (RGB) data producer to an image signal for causing an image for guiding spots for acupuncture, to be displayed on a monitor, said video signal transformation creating said image signal to further cause a level display as part of said image for guiding spots for acupuncture, to be displayed on the monitor as follows:

an initial display of a guiding program of spots for acupuncture according to a control signal by a user;

stimulation details according to a control signal by a user;

image information about spots for acupuncture in a palm according to a control signal by a user; and an acupuncture shape which moves into pre-established spots of said image in order, changing its color when yumpa therapy is selected as an acupuncture therapy.

2. A device for guiding spots for acupuncture according to claim 1, wherein contents of said initial display are provided by selective combination of a body, persons who need an acupuncture cure, and a first aid item.

3. A device for guiding spots for acupuncture according to claim 1, wherein said video signal transformation creates said image signal to display various acupuncture therapies and cure messages corresponding to said spots for acupuncture on said monitor, along with said image information.

4. A device for guiding spots for acupuncture according to claim 3, wherein said video signal transformation creates said image signal to selectively display said acupuncture therapies selected from the group consisting of acupuncture needles, moxibustion, pellets and yumpa therapy.

5. A device for guiding spots for acupuncture comprising:

a central processing unit (CPU) for controlling storage and output of data according to a control signal by a user;

a first storage unit, connected with said CPU and including data stored therein for guiding spots for acupuncture, for outputting said stored data according to a control signal of said CPU;

a character data producer for outputting character data according to a control of said CPU;

a RED GREEN BLUE (RGB) data producer for transforming data output by said first storage unit to image data according to a control of said CPU; and a video signal transformation for transforming output signals of said character data producer and said RED GREEN BLUE (RGB) data producer to an image signal for causing an image for guiding spots for acupuncture, to be displayed on a monitor, said video signal transformation creating said image signal to further cause the following to be displayed on the monitor as part of said image for guiding spots for acupuncture:

a level display for displaying an initial display of a guiding program of spots for acupuncture according to a control signal by a user;

a level display for displaying stimulation details according to a control signal by a user;

a level display for displaying image information about spots for acupuncture in a palm according to a control signal by a user;

various acupuncture therapies and cure messages corresponding to said spots for acupuncture such that said acupuncture therapies are selected from the group consisting of acupuncture needles, moxibustion, pellets and yumpa therapy; and an acupuncture shape which moves into pre-established spots of said image in order, changing its color when said yumpa therapy is selected.

6. A method for guiding spots for acupuncture, comprising the steps of:

controlling storage and output of data according to a control signal by a user by means of a central processing unit (CPU);

storing data in a first storage unit connected with said CPU for storing data for guiding spots for acupuncture and for outputting said stored data according to a control signal of said CPU;

outputting character data by a character data producer according to control of said CPU;

transforming data output by said first storage unit to image data according to a control of said CPU with a RED GREEN BLUE (RGB) data producer; and creating an image signal in response to said character data and said transformed data in a video signal transformation for causing an image for guiding spots for acupuncture, to be displayed on a monitor, said image signal causing a level display as part of said image for guiding spots for acupuncture, to be displayed as follows on the monitor:

an initial display of a guiding program of spots for acupuncture according to a control signal by a user;

stimulation details according to a control signal by a user;

image information about spots for acupuncture in a palm according to a control signal by a user; and an acupuncture shape which moves into pre-established spots of said image in order, changing its color when yumpa therapy is selected as an acupuncture therapy.

* * * * *